United States Patent [19]
Soff et al.

[11] Patent Number: 5,801,012
[45] Date of Patent: Sep. 1, 1998

[54] METHODS AND COMPOSITIONS FOR GENERATING ANGIOSTATIN

[75] Inventors: Gerald Soff, Skokie; Stephen T. Gately, Palatine; Przemyslaw Twardowski, Chicago, all of Ill.

[73] Assignee: Northwestern University, Evanston, Ill.

[21] Appl. No.: 710,305

[22] Filed: Sep. 17, 1996

[51] Int. Cl.$^6$ .............................. C12N 9/50; C12N 9/48; C12N 9/00; C12P 21/06

[52] U.S. Cl. ................... 435/68.1; 435/212; 435/183; 435/69.6; 435/219

[58] Field of Search ..................... 435/68.1, 69.6, 435/219, 212, 183

[56] References Cited

FOREIGN PATENT DOCUMENTS

WO 95/29242  11/1995  WIPO .

OTHER PUBLICATIONS

O'Reilly et al. Cell. 79:315–28, 1994, Oct. 21, 1994.
O'Reilly et al. Cold Spr. Harb. Symp. Quant. Biol. 59:471–482, 1994.
Chen et al. Cancer Res. 55:4230–33, 1995, Oct. 1, 1995.
Castellino et al. Meth. Enzymol. 80:365–378, 1981.
Battegay, "Angiogenesis: Mechanistic Insights, Neovascular Diseases, And Therapeutic Prospects," *J. Mol. Med.*, vol. 73, pp. 333–346 (1995).
Brem et al., "Inhibition Of Angiogenesis And Tumor Growth In The Brain," *American Journal of Pathology*, vol. 137, No. 5, pp. 1121–1142 (1990).
Brem, et al., "Placebo-controlled Trial Of Safety And Efficacy Of Intraoperative Controlled Delivery By Biodegradable Polymers Of Chemotherapy For Recurrent Gliomas," *Lancet*, vol. 345, pp. 1008–1012 (1995).
Castellino & Powell, "Human Plasminogen," *Methods Enzymol*, vol. 80, 365–78 (1981).
Chen et al., "A Strategy To Discover Circulating Angiogenesis Inhibitors Generated by Human Tumors," *Cancer Research*, vol. 55, pp. 4230–4233 (1995).
Dameron et al., "Control Of Angiogenesis In Fibroblasts By p53 Regulation Of Thrombospondin-1," *Science*, vol. 265, 1582–1584 (1994).
Dong et al., "Generation Of The Angiogenesis Inhibitor, Angiostatin, By Lewis Lung Carcinoma Is Mediated By Macrophase Elastase," *Proc. Am. Assoc. Cancer Res.*, vol. 37 p. 58 (1996).

Folkman & Shing, "Angiogenesis," *J. Biol. Chem*, vol. 267, pp. 10931–10934 (1992).
Heussen & Dowdle, "Electrophoretic Analysis Of Plasminogen Activators In Polyacrylamide Gels Containing Sodium Dodecyl Sulfate And Copolymerized Substrates," *Anal. Biochem.*, vol. 102, 196–202 (1980).
Hourani et al., "Inhibition Of S-91 Mouse Melanoma Metastases And Growth By D-Penicillamine," *Laboratory Investigation*, vol. 21, No. 5, pp. 434–438 (1969).
Laemmli, "Cleavage Of Structural Proteins During The Assembly Of The Head Of Bacteriophase T4," *Nature*, vol. 227, pp. 680–685 (1970).
Littman et al., "Acceleration Of Growth Of Sarcoma 180 With Pyridoxamine And Retardation With Penicillamine," *P.S.E.B.M.*, vol. 113, pp. 667–674 (1963).
Matsubara et al., "Inhibition Of Human Endothelial Cell Proliferation In Vitro And Neovascularization In Vivo By D-Penicillamine," *J. Clin. Invest.*, vol. 83, pp. 158–167 (1989).
O'Reilly et al., "Angiostatin Induces And Sustains Dormancy Of Human Primary Tumors In Mice," *Nature Med.* vol. 2, 689–692 (1996).
O'Reilly et al., "Angiostatin: A Novel Angiogenesis Inhibitor That Mediates The Suppression Of Metastases By A Lewis Lung Carcinoma," *Cell*, vol. 79, 315–328 (1994).
Polverini et al., "Assay And Purification Of Naturally Occurring Inhibitor Of Angiogenesis," *Methods Enzymol*, vol. 198, pp. 440–450 (1991).
Schnaper et al., "Type IV Collagensae(s) And TIMPs Modulate Endothelial Cell Morphogenesis In Vitro," *J. Cell. Physiol*, vol. 156, pp. 235–246 (1993).
Sottrup–Jensen et al., "The Primary Structure Of Human Plasminogen: Isolation Of Two Lysine–Binding Fragments And One Mini–Plasminogen (MW, 38,000) By Elastase–Catalyzed–Specific Limited Proteolysis," *Progress in Chemical Fibrinolysis and Thrombolysis*, vol. 3, pp. 191–209 (1978).
Takano et al., "Suramin, An Anticancer And Angiosuppressivie Agent, Inhibits Endothelial Cell Binding Of Basic Fibroblast Growth Factor, Migration, Proliferation, And Induction Of Urokinase–Type Plasminogen Activator," *Cancer Res.*, vol. 54, pp. 2654–2660 (1994).

*Primary Examiner*—Lila Feisee
*Assistant Examiner*—Ray F. Ebert
*Attorney, Agent, or Firm*—Sheridan Ross P.C.

[57] ABSTRACT

The invention provides a method of generating angiostatin in vitro comprising contacting plasminogen or plasmin with a plasminogen activator and a sulfhydryl donor.

4 Claims, 10 Drawing Sheets

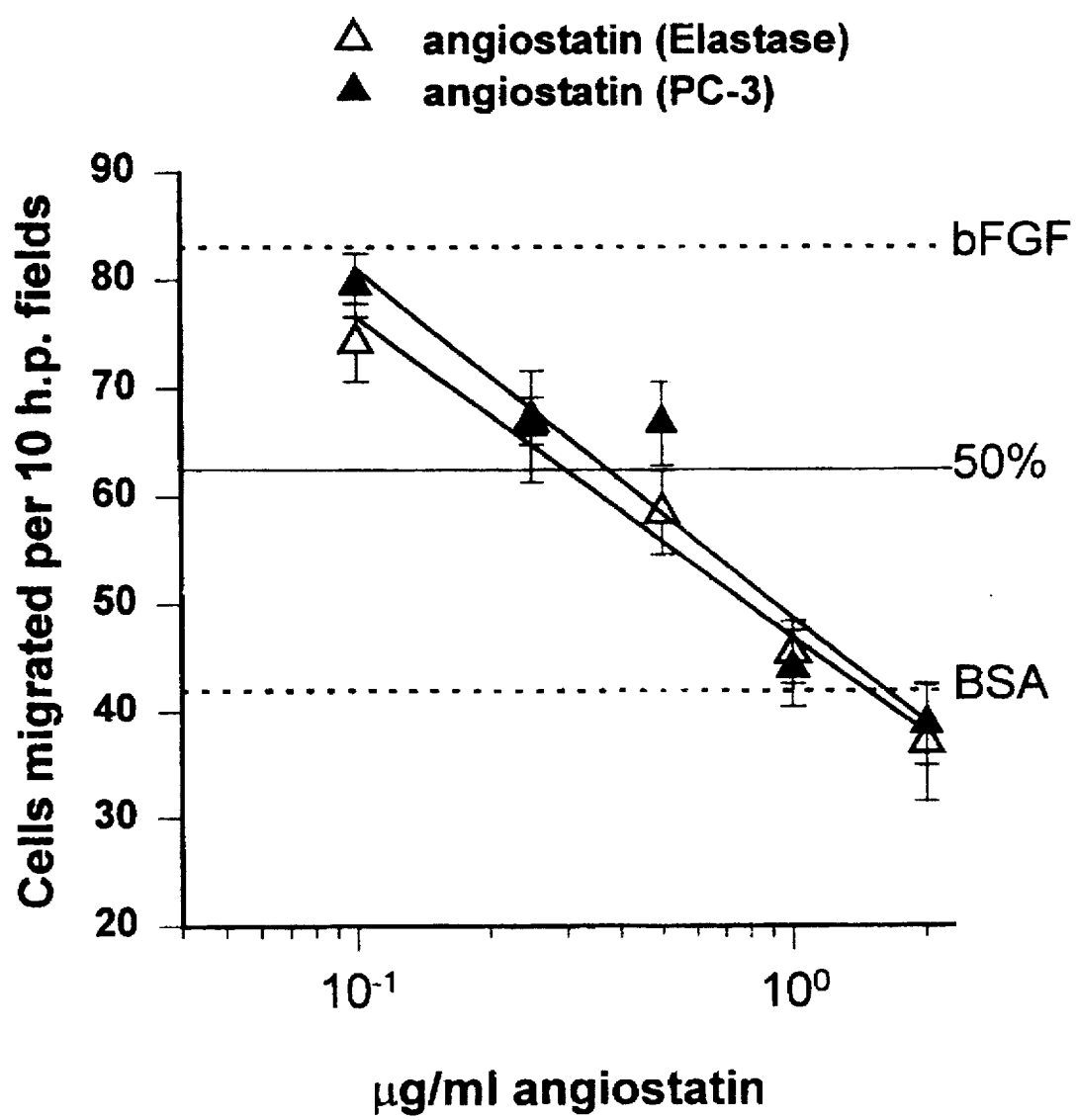

METHODS AND COMPOSITIONS FOR GENERATING ANGIOSTATIN

FIELD OF THE INVENTION

This invention relates to methods and compositions for making angiostatin, an inhibitor of angiogenesis. The invention also relates to the treatment of diseases caused by, or involving, angiogenesis.

BACKGROUND OF THE INVENTION

Angiostatin, a proteolytic fragment of plasminogen including kringles 1 though 4, is a potent inhibitor of angiogenesis and the growth of tumor cell metastases. O'Reilly et al., *Cell*, 79, 315–328 (1994). Angiostatin is found in vivo in tumor-bearing mice. O'Reilly et al., *Cell*, 79, 315–328 (1994); O'Reilly et al., *Nature Med.* 2, 689–692 (1996). The enzymatic mechanism by which angiostatin is generated in vivo remains unknown.

Angiostatin activity can be generated in vitro by limited elastase proteolysis of plasminogen. Sottrup-Jensen et al., in *Progress in Chemical Fibrinolysis and Thrombolysis*, 3, 191–209 (Davidson et al. eds. 1978). A recent abstract proposes that angiostatin is generated by macrophages infiltrating primary tumors and releasing elastase activity, which then cleaves plasminogen to form a protein having angiostatin activity. Dong et al., *Proc. Am. Assoc. Cancer Res.*, 37 58 (1996). However, while limited elastase cleavage of plasminogen will yield a fragment or fragments having angiostatin activity, elastase will further digest the fragment(s) to inactive peptides, and therefore, is probably not the enzyme that generates angiostatin in vivo.

As noted above, angiostatin may be generated in vitro by limited elastase proteolysis of plasminogen. This method has several disadvantages. First, while elastase cleaves plasminogen to generate a fragment containing kringles 1–3, it is not known if this cleavage is at the normal sites where cleavage occurs to produce angiostatin in vivo. Therefore, the elastase-derived angiostatin may have altered in vivo processing with altered activity in humans. It may also be immunogenic if the sites of peptide cleavage are different from normal angiostatin.

A second means of producing angiostatin is by expressing the desired kringle 1–4 domains, or subdomains or other domains, of the plasminogen cDNA or gene in an expression vector in prokaryotic or eukaryotic cells. See PCT application WO 95/29242. This approach is also limited since the appropriate domains to express are not known. The product may also be immunogenic and may not be processed in humans as would be the product generated by cleavage of plasminogen by the normal in vivo enzymes.

Finally, angiostatin can be isolated from the body fluids of animals in which it is produced. See PCT application WO 95/29242. However, angiostatin cannot be produced in sufficient quantities for disease treatment in this manner, and the angiostatin may be contaminated with infectious agents when isolated from such sources.

Clearly a need exists for a method of producing native angiostatin in large quantities. "Native angiostatin" is defined herein to be the angiostatin produced in vivo or angiostatin, no matter how produced, which is the same as the angiostatin produced in vivo.

SUMMARY OF THE INVENTION

The present invention provides such a method. In particular, the invention provides a method of generating angiostatin in vitro comprising contacting plasminogen or plasmin with a plasminogen activator and a sulfhydryl donor. It has been found that a conditioned culture medium (CCM) produced by culturing cancer cells, primary endothelial cells, smooth muscle cells or fibroblasts produces angiostatin when contacted with plasminogen or plasmin. The active factors in the CCM have been identified to be a plasminogen activator and a sulfhydryl donor. Thus, the angiostatin produced by the use of a plasminogen activator and sulfhydryl donor is the same as angiostatin produced in vivo, i.e., it is native angiostatin.

The angiostatin produced by the method of the invention, along with the rest of the reaction medium, or angiostatin purified or partially purified from the reactants, may be administered to an animal, including a human, in need thereof. Animals in need of angiostatin are animals suffering from an angiogenic disease.

The invention further provides a composition for generating angiostatin. The composition comprises a sulfhydryl donor and a plasminogen activator. The composition may be CCM produced by culturing cells capable of producing plasminogen activator, or a lysate of such cells.

The invention also provides a method of treating an angiogenic disease comprising administering to an animal suffering from such a disease an amount of a sulfhydryl donor effective to cause the conversion of plasminogen or plasmin to angiostatin by plasminogen activator. The plasminogen, plasmin and plasminogen activator may be those found endogenously in the animal or, preferably, effective amounts of the plasminogen, plasmin and/or plasminogen activator are also administered to the animal.

The invention further provides a container holding a plasminogen activator, alone or in combination with sulfhydryl donor. The container has a label thereon instructing administration of the plasminogen activator or the combination of the plasminogen activator and sulfhydryl donor to an animal suffering from an angiogenic disease. The invention also provides a container holding a sulfhydryl donor with a label thereon instructing administration of the sulfhydryl donor in an amount effective to cause the conversion of plasminogen or plasmin to angiostatin by plasminogen activator.

BRIEF DESCRIPTION OF THE DRAWINGS

FIGS. 3A-B: Graphs showing that angiostatin produced by incubating plasminogen with PC-3 SCFM inhibits in vitro steps critical for angiogenesis. FIG. 3A: Endothelial cell proliferation. The data are mean ± standard deviation. FIG. 3B: Basic fibroblast growth factor (bFGF)-induced migration. Background migration without the inducer and in the presence of stimulatory bFGF are indicated. Toxicity was measured in parallel by trypan blue exclusion and was <10% at all concentrations.

FIG. 4A: Control HUVEC form branching, interconnecting networks. FIG. 4B: By contrast angiostatin produced using PC-3 SFCM caused a significant disruption of the tube network.

FIG. 5A: A hydron pellet (indicated by the arrow) containing bFGF induced a positive neovascular response 7 days after implantation. FIG. 5B: By contrast, no vessels are observed approaching a hydron pellet containing bFGF and 10 µg/ml angiostatin produced using PC-3 SFCM (indicated by the arrow).

DETAILED DESCRIPTION OF THE PRESENTLY PREFERRED EMBODIMENTS

Figure 1A:
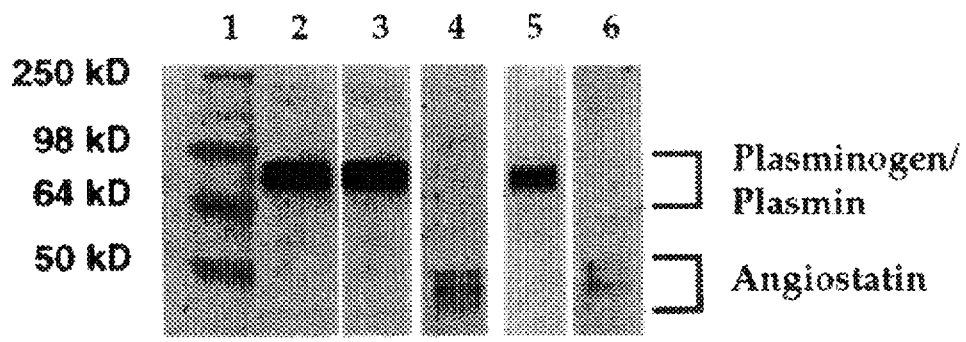
FIG. 1A: Western blot showing conversion of plasminogen and plasmin to angiostatin by serum-free conditioned medium (SFCM) produced by PC-3 cells. Lane 1, molecular weight standard; lane 2, human plasminogen; lane 3, human plasminogen incubated overnight at 37° C. in non-conditioned RPMI; lane 4, human plasminogen incubated overnight at 37° C. in SFCM from PC-3 cells; lane 5, human plasmin incubated in non-conditioned RPMI; lane 6, human plasmin incubated in SFCM produced by PC-3 cells.

The invention provides an in vitro method of generating native angiostatin. The method comprises contacting plasminogen or plasmin with a plasminogen activator and a sulfhydryl donor.

The plasminogen may be from any animal species. Preferably, however, plasminogen from the species of animal to be treated with the angiostatin is used to avoid immune reactions upon administration of the angiostatin. Thus, if a human is to be treated with the angiostatin, human plasminogen is preferably used.

Methods of making plasminogen are well known in the art. Plasminogen may also be purchased commercially. Preferably the plasminogen is prepared by recombinant DNA or other techniques that avoid the inclusion of infectious agents in the plasminogen preparation.

Plasmin may also be used to prepare angiostatin. Plasmin may be prepared from plasminogen by methods known in the art. Plasmin may also be purchased commercially.

All types of plasminogen activators may be used to convert plasminogen and plasmin to angiostatin, including urokinase-type plasminogen activators, tissue-type plasminogen activators and streptokinase. The plasminogen activator may be from any animal species. Methods of making plasminogen activators are well known in the art and many plasminogen activators are available commercially. Preferably the plasminogen activator is prepared by recombinant DNA or other techniques that avoid the inclusion of infectious agents in the plasminogen activator preparation.

Any sulfhydryl donors may be used for converting plasminogen and plasmin to angiostatin. Sulfhydryl donors are well known and are available commercially. Suitable sulfhydryl donors include L-cysteine, D-cysteine, DL-cysteine, N-acetyl-L-cysteine, reduced glutathione, D-penicillamine and captopril. The sulfhydryl donor is believed to reduce or alter disulfide bond formation in one of the reactants (plasminogen, plasmin or plasminogen activator) and/or the product(s) (angiostatin or an intermediate).

The plasminogen or plasmin is contacted with the plasminogen activator and sulfhydryl donor in amounts and under conditions effective to cause the conversion of the plasminogen or plasmin to angiostatin. These amounts and conditions can be determined empirically as is known in the art. In particular, from about 1 ng/ml to about 1 μ/ml of urokinase plasminogen activator and from about 10 μM to about 1 mM of sulfhydryl donor for each microgram of plasminogen or plasmin in a 1 ml reaction have been found to give complete conversion to angiostatin after about 24 hours of incubation at 37° C.

The invention further provides a composition for generating angiostatin from plasminogen or plasmin. The composition comprises a plasminogen activator and a sulfhydryl donor as described above. The plasminogen activator and sulfhydryl donor may be contained in any physiologically-acceptable solution (e.g., saline, buffers, culture medium) or may be present in crystalline or lyophilized form. Compositions suitable for therapeutic use are described below.

The composition may be a conditioned culture medium (CCM) prepared by culturing cells capable of producing plasminogen activator. Malignant animal cells, human and non-human, which express a plasminogen activator can produce CCM capable of converting plasminogen and plasmin into angiostatin. Suitable malignant cells include human prostate carcinoma cell lines PC-3, DU-145, LN-CaP, human breast carcinoma cell lines MDA-MB-231 and MCF-7, human glioma cell lines U-373, U-118, A-172, and U-87, and mouse melanoma cell line B16F10. Many non-malignant animal cells are known to produce plasminogen activator. Suitable non-malignant cells include primary endothelial cells (e.g., bovine aortic endothelial cells), smooth muscle cells (e.g., bovine smooth muscle cells), and fibroblasts. In addition, bacterial cells are known which produce plasminogen activator (e.g., streptokinase), and cells of any type can be transformed by recombinant DNA techniques to produce plasminogen activator. Suitable cells and cell lines are well known in the art and may be obtained commercially, from cell depositories, and by methods well known in the art.

Suitable culture conditions for these cells are also well known in the art. The culture medium used must contain a sulfhydryl donor, or a sulfhydryl donor may be added to the CCM after it is produced. Suitable culture media include those available commercially, such as RPMI, DMEM, etc. The CCM may be produced by simply culturing the cells under normal culture conditions for a sufficient time to produce CCM capable of converting plasminogen or plasmin to angiostatin. This time can be determined empirically. In particular, it has been found that culturing the mammalian cells for 24–72 hours after a monolayer has formed at 37° C. is sufficient.

Alternatively, or in addition, the cells can be lysed after culturing for a time sufficient to allow synthesis of plasminogen activator. This time can be determined empirically, but culturing the cells until a monolayer has formed should be sufficient. The lysate can be used to convert plasminogen and plasmin to angiostatin.

The angiostatin produced by the method of the invention may be purified from the reaction mixture. Methods of protein purification are well known in the art. In particular, angiostatin may be purified by affinity chromatography using lysine-Sepharose. Residual plasmin activity should be removed with, e.g., soybean trypsin inhibitor-Sepharose, aprotinin-Sepharose, or other affinity chromatography procedures that remove serine proteases or the plasmin catalytic domain.

The angiostatin produced by the method of the invention has been found to have the N-terminal sequence of plasmin. For angiostatin produced from human plasminogen, the N-terminal sequence has been found to be Lys Val Tyr Leu Ser Glu Cys Lys Thr Gly [SEQ ID NO: 1]. Its C-terminal sequence has not yet been determined. The angiostatin reacts with a monoclonal antibody specific for kringles 1–3 of plasminogen and has a molecular weight of about 50 kD as determined by polyacrylamide gel electrophoresis under non-reducing conditions. It inhibits angiogenesis, as assessed by a variety of tests in vitro and in vivo.

The invention also provides methods of treating an angiogenic disease. An angiogenic disease is one caused by, involving or dependent on angiogenesis. Angiogenic diseases include neoplastic diseases (e.g., tumors and tumor metastasis), benign tumors (e.g., hemangiomas, acoustic neuromas, neurofibromas, trachomas, pyrogenic granulomas), connective tissue disorders (e.g., rheumatoid arthritis and atherosclerosis), ocular angiogenic diseases (e.g., diabetic retinopathy, retinopathy of prematurity, macular degeneration, corneal graft rejection, neovascular glaucoma, retrolental fibroplasia, rubeosis), cardiovascular diseases, cerebral vascular diseases, diabetes-associated diseases and immune disorders (e.g., chronic inflammation and autoimmunity).

The angiogenic disease may be treated by administering an effective amount of the angiostatin produced by the method of the invention. The angiogenic disease may also be treated by administering an amount of a sulfhydryl donor sufficient to cause conversion of plasminogen or plasmin to angiostatin by plasminogen activator. The plasminogen, plasmin and plasminogen activator may be those found endogenously in the animal or, preferably, effective amounts of plasminogen, plasmin and/or plasminogen activator are also administered to the animal. Animals treatable according to the invention include mammals, such as dogs, cats, other domestic animals, and humans.

Effective dosage forms, modes of administration and dosage amounts for the various compounds for treating angiogenic diseases may be determined empirically, and making such determinations is within the skill of the art. It is understood by those skilled in the art that the dosage amount will vary with the activity of the particular compound employed, the severity of the angiogenic disease, the route of administration, the rate of excretion of the compound, the duration of the treatment, the identify of any other drugs being administered to the animal, the age, size and species of the animal, and like factors known in the medical and veterinary arts. In general, a suitable daily dose of a compound of the present invention will be that amount of the compound which is the lowest dose effective to produce a therapeutic effect. However, the daily dosage will be determined by an attending physician or veterinarian within the scope of sound medical judgment. If desired, the effective daily dose may be administered as two, three, four, five, six or more sub-doses, administered separately at appropriate intervals throughout the day.

The compounds of the present invention may be administered to an animal patient for therapy by any suitable route of administration, including orally, nasally, rectally, vaginally, parenterally (e.g., intravenously, intraspinally, intraperitoneally, subcutaneously, or intramuscularly), intracisternally, transdermally, intracranially, intracerebrally, and topically (including buccally and sublingually). The preferred routes of administration are orally and intravenously. The use of biodegradable polymers similar to that described by Brem, et al., *Lancet*, 345, 1571 (1995) for the local sustained release of pharmacological agents following incorporation into the biodegradable polymers is also a preferred method of administration. Implantation of the drug-impregnated polymer at, e.g., a tumor site, allows prolonged local exposure with minimal systemic exposure.

While it is possible for a compound of the present invention to be administered alone, it is preferable to administer the compound as a pharmaceutical formulation (composition). The pharmaceutical compositions of the invention comprise a compound of the invention as an active ingredient in admixture with one or more pharmaceutically-acceptable carriers and, optionally, with one or more other compounds, drugs or other materials. Each carrier must be "acceptable" in the sense of being compatible with the other ingredients of the formulation and not injurious to the patient.

Pharmaceutical formulations of the present invention include those suitable for oral, nasal, ophthalmic, topical, rectal, vaginal and/or parenteral administration. Regardless of the route of administration selected, the compounds of the present invention are formulated into pharmaceutically-acceptable dosage forms by conventional methods known to those of skill in the art.

The amount of active ingredient which will be combined with a carrier material to produce a single dosage form will vary depending upon the host being treated, the particular mode of administration and all of the other factors described above. The amount of active ingredient which will be combined with a carrier material to produce a single dosage form will generally be that amount of the compound which is the lowest dose effective to produce a therapeutic effect or the maximally-tolerated dose that yields a therapeutic increment for life-threatening illnesses, such as cancer.

Methods of preparing pharmaceutical formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, powders, granules or as a solution or a suspension in an aqueous or non-aqueous liquid, or an oil-in-water or water-in-oil liquid emulsions, or as an elixir or syrup, or as pastilles (using an inert base, such as gelatin and glycerin, or sucrose and acacia), and the like, each containing a predetermined amount of a compound of the present invention as an active ingredient. A compound of the present invention may also be administered as bolus, electuary or paste.

In solid dosage forms of the invention for oral administration (capsules, tablets, pills, dragees, powders, granules and the like), the active ingredient is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar—agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monosterate; (8) absorbents, such as kaolin and bentonite clay; (9) lubricants, such as talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may be employed as fillers in soft and hard-filled gelatin capsules using such excipients as lactose or milk sugars, as well as high molecular weight polyethylene glycols and the like.

A tablet may be made by compression or molding optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter. These compositions may also optionally contain opacifying agents and may be of a composition that they release the active ingredient only, or preferentially, in a certain portion of the gastrointestinal tract, optionally, in a delayed manner. Examples of embedding compositions which can be used include polymeric substances and waxes. The active ingredient can also be in microencapsulated form.

Liquid dosage forms for oral administration of the compounds of the invention include pharmaceutically-acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar—agar and tragacanth, and mixtures thereof.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or salicylate, and which is solid at room temperature, but liquid at body temperature and, therefore, will melt in the rectum or vaginal cavity and release the active compound. Formulations of the present invention which are suitable for vaginal administration also include pessaries, tampons, creams, gels, pastes, foams or spray formulations containing such carriers as are known in the art to be appropriate.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically-acceptable carrier, and with any buffers, or propellants which may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder or mixtures of these substances. Sprays can additionally contain customary propellants such as chlorofluorohydrocarbons and volatile unsubstituted hydrocarbons, such as butane and propane.

Transdermal patches have the added advantage of providing controlled delivery of a compound of the invention to the body. Such dosage forms can be made by dissolving, dispersing or otherwise incorporating a compound of the invention in a proper medium, such as an elastomeric matrix material. Absorption enhancers can also be used to increase the flux of the compound across the skin. The rate of such flux can be controlled by either providing a rate-controlling membrane or dispersing the compound in a polymer matrix or gel.

Pharmaceutical compositions of this invention suitable for parenteral administrations comprise one or more compounds of the invention in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as wetting agents, emulsifying agents and dispersing agents. It may also be desirable to include isotonic agents, such as sugars, sodium chloride, and the like in the compositions. In addition, prolonged absorption of the injectable pharmaceutical form may be brought about by the inclusion of agents which delay absorption such as aluminum monosterate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug from is accomplished by dissolving or suspending the drug in an oil vehicle.

Injectable depot forms are made by forming microencapsule matrices of the drug in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue. The injectable materials can be sterilized for example, by filtration through a bacterial-retaining filter.

The formulations may be presented in unit-dose or multi-dose sealed containers, for example, ampoules and vials, and may be stored in a lyophilized condition requiring only the addition of the sterile liquid carrier, for example water for injection, immediately prior to use. Extemporaneous injection solutions and suspensions may be prepared from sterile powders, granules and tablets of the type described above.

Since the invention provides, for the first time, a method of producing large quantities of native angiostatin, the amino acid sequence of native angiostatin can finally be determined. Once this is accomplished, native angiostatin can be made by recombinant DNA techniques. DNA coding for native angiostatin can also be used for gene therapy, so that native angiostatin can be produced in vivo in animals suffering from angiogenic diseases. Recombinant DNA techniques and gene therapy techniques are well known in the art. See, e.g., PCT WO 95/29242, the complete disclosure of which is incorporated herein by reference.

EXAMPLES

Example 1: Preparation of Conditioned Medium Containing Plasminogen-Angiostatin Converting Activity (PACA)

This example demonstrates that a variety of cells express enzymatic activity that can generate bioactive angiostatin from purified human plasminogen or plasmin. Affinity-purified angiostatin generated by incubating plasminogen or plasmin with serum-free conditioned medium (SFCM) inhibited human endothelial cell proliferation, migration induced by angiogenic factor basic fibroblast growth factor (bFGF), endothelial cell tube formation, and bFGF-induced corneal angiogenesis. Serine proteinase inhibitors, but not inhibitors of metallo-, cysteine, or aspartic proteinases, blocked angiostatin generation. Elastatinal, a specific inhibitor of elastase, failed to block angiostatin generation, indicating that an elastase is not responsible for the conversion of plasminogen to angiostatin. Instead, the data show that serine proteinase activity is necessary for angiostatin generation.

A. Methods

1. Cell Culture. The human umbilical vein endothelial cells (HUVEC), were grown in RPMI supplemented with 20% bovine calf serum (Hyclone Laboratories Inc., Logan Utah #A-2151-L), 100 U/ml penicillin G, 100 mg/ml streptomycin, L-glutamine, (Gibco BRL), 2500 U Sodium heparin (Fisher Scientific, Itasca, Ill.), and 50 mg/ml endothelial cell growth supplement (Collaborative Biomedical Research, Bedford, Mass.). The other cells listed in Table 1 were grown in RPMI-1640 supplemented with 10% fetal bovine serum, 100 U/ml penicillin G, 100 mg/ml streptomycin (Gibco BRL, Gaithersburg, Md.). Cells were maintained at 37° C. in a humidified incubator in an atmosphere of 5% $CO_2$. To generate SFCM, confluent cell monolayers were washed twice with phosphate buffered saline, then serum-free RPMI was added. The next day the SFCM was collected and centrifuged at 3000 rpm for 15 minutes to remove insoluble cellular debris.

2. Angiostatin Generation. Two micrograms of human plasminogen, obtained by lysine-sepharose affinity chromatography of human plasma (Castellino & Powell, *Methods Enzymol*, 80, 365–78 (1981)), or human plasmin (#527624, Calbiochem-Novabiochem Corp., La Jolla, Calif.) were added to 100 μl aliquots of SFCM and the mixture incubated at 37° C. overnight. Aliquots were analyzed for angiostatin generation by western blot (see below). Plasminogen cleavage by SFCM was also assessed in the presence of proteinase inhibitors (Boehringer Mannheim, Indianapolis, Ind.).

3. Western Blot. Samples were electrophoresed under non-reducing conditions on 12% polyacrylamide gels (NOVEX, San Diego, Calif.) in Tris-Glycine running buffer (Laemmli, *Nature*, 227, 680–685 (1970)), and electrotransferred to a 0.45 μM polyvinylene difluoride (PVDF) membrane (Immobilon, Millipore, Bedford, Mass.). The membrane was then blocked for 30 minutes in blocking buffer (1% bovine serum albumin in Tris-buffered saline) and probed with a 1:1000 dilution of a monoclonal antibody to the kringles 1–3(K1–3) fragment of human plasminogen (VAP 230L, Enzyme Research Laboratories, Inc., South Bend, Ind.). Following washing, the membrane was incubated for 30 minutes with an alkaline phosphatase conjugated goat anti-mouse IgG secondary antibody (Kirkegaard & Perry Laboratories (KPL), Gaithersburg, Md.) and developed using 5-bromo-4-chloro-3-indoyl-phosphate/nitroblue tetrazolium (KPL).

4. Zymographic Analysis. Zymograms to detect matrix metalloproteinase activity were performed as described previously. Heussen & Dowdle, *Anal. Biochem.*, 102, 196–202 (1980).

5. Chromogenic Peptide Substrates. To determine if an elastase was present, 50 μl of SFCM were incubated with 0.3 mM of chromogenic peptide substrates specific for elastase (substrate I, MeOSuc-Ala-Ala-Pro-Val-pNA; substrate II, Boc-Ala-Ala-Pro-Ala-pNA); substrate III, pGlu-Pro-Val-pNA; substrate IV, Suc-Ala-Ala-Pro-Abu-pNA) (Calbiochem-Novabiochem Corp.), at 37° C. for 2–18 hours. Substrate cleavage was determined by monitoring the absorbance at 405 nm (Molecular Devices, Menlo Park, Calif.).

6. Lysine-Sepharose Purification of Angiostatin. To generate purified angiostatin for bioactivity analyses, human plasminogen was incubated with PC-3 SFCM at 20 μ/ml overnight at 37° C. The reaction product was applied to a lysine-sepharose column (Pharmacia Biotech), pre-equilibrated with TBS (50 mM Tris, pH 7.5, and 150 mM NaCl) Following washes with TBS to remove non-specifically bound protein, angiostatin was eluted in 0.2 M epsilon aminocaproic acid (EACA) in TBS. The eluted fraction was dialyzed (molecular weight cut off 12,000–14,000) to phosphate buffered saline. To remove residual plasmin, the angiostatin was applied to a soybean trypsin inhibitor agarose (Sigma Chemical Co., St. Louis, Mo.) column, and the flow-through collected, filter-sterilized and stored at −80° C. until used. Angiostatin was quantitated by measuring the absorbance at 280 nm, using an $A^{1\%}/_{1cm}$ of 8.0. Sottrup-Jensen et al., in *Progress in Chemical Fibrinolysis and Thrombolysis*, vol. 3, pages 191–209 (Davidson et al. eds. 1978). The purified angiostatin was also examined by Coomassie brilliant blue staining of polyacrylamide gels, and immunodetection by western blot. Elastase-generated angiostatin, purified from human plasma as described in O'Reilly, et al., *Nature Med.*, 2, 689–692 (1996), was a generous gift from M.S. O'Reilly, Children's Hospital, Harvard University, Boston, Mass.

7. Microsequence Analysis of Angiostatin. To determine the $NH_2$-terminus of the angiostatin bands, 10 μg/ml of the affinity-purified angiostatin prepared by incubating plasminogen with PC-3 SFCM was electrophoresed on a 12% SDS-polyacrylamide gel, electroblotted to a PVDF membrane, and stained with Coomassie blue. The bands were excised, placed on Porton sample support discs, and sequenced using a pulse liquid-phase sequencer with phenylthiohydantoin analysis.

8. Endothelial Cell proliferation Assay. Cell proliferation was determined utilizing the CellTiter 96™ AQ Non-Radioactive Cell Proliferation Assay (Promega Corp., Madison, Wis.). The human endothelial cells were plated in a 96-well tissue culture plates (Becton Dickinson, Lincoln Park, N.J.) at a concentration of $5.0 \times 10^3$ cells/well. The following day, 1, 5, 8, or 10 μg/ml of angiostatin in fresh medium was added to triplicate wells. Wells without angiostatin served as control. The cells were incubated for 72 hours, and an absorbance read at 490 nm, reflecting the number of proliferating cells, was measured using an automated microplate reader (Molecular Devices). The results are reported as the percent of non-treated control cell number.

9. Endothelial Cell Migration Assay. To determine the ability of angiostatin prepared by incubation of plasminogen with PC-3 SFCM to block migration of endothelial cells towards an angiogenic factor, bFGF, migration assays were performed in a modified Boyden chamber using bovine capillary endothelial cells (a kind gift of Dr. Folkman, Harvard Medical School, Boston, Mass.) as described previously. Dameron et al., *Science*, 265, 1582–84 (1994). Cells were grown in Dulbecco's modified Eagle's medium (DMEM) with 10% donor calf serum and 100 mg/ml endothelial cell mitogen and used at passage 15. To assess migration, the cells were serum starved overnight in DMEM supplemented with 0.1% bovine serum albumin (BSA), harvested, suspended in DMEM/BSA, plated at $10^6$/ml on the lower surface of a gelatinized membrane (Nucleopore Corp., Plesanton, Calif.) in an inverted Boyden chamber, and incubated for 1.5–2 hours to allow cell attachment. The chambers were reinverted, test material was added to the top well, and the chamber incubated for an additional 3–4 hours. Membranes were then fixed and stained and the number of cells that migrated to the top of the filter in 10 high-power fields was determined. DMEM with 0.1% BSA was used as a negative control, and bFGF (provided by Dr. Noel Bouck and prepared as described in Dameron et al., *Science*, 265, 1582–1584 (1994)) at 10 ng/ml was used as a positive control.

10. Endothelial Cell Tube Formation. HUVEC were plated on gels of Matrigel (kindly provided by Hynda Kleinman, National Institute of Dental Research) in 24-well tissue culture plates as described previously. Schnaper et al., *J. Cell. Physiol*, 156, 235–246 (1993). Angiostatin, prepared by incubation with PC-3 SFCM, in non-conditioned RPMI was added to the wells, followed by cells at a final concentration of $4.0 \times 10^4$ cells in 1 ml of 50% HUVEC culture medium, 50% RPMI. Each angiostatin or control condition was assayed in triplicate. The cultures were incubated for 16–18 hours at 37° C., in a 5% $CO_2$ humidified atmosphere, then fixed with Diff-Quick Solution II (Baxter, McGraw Park, Ill.). A representative area of the tube network was photographed using a Polaroid MicroCam camera at a final magnification of 35×. The photographs were then quantitated by a blinded observer who measured the length of each tube, correcting for portions of tubes that were incomplete. The total length of the tubes was determined for each photograph and the mean tube length was determined. The results were expressed as the mean ± standard error of the mean.

11. Corneal Angiogenesis Assay. The corneal assay was performed as described previously. Polverini et al., *Methods Enzymol*, 198, 440–450 (1991). Briefly, 5 μl hydron pellets (Hydron Laboratories, New Brunswick, N.J.) containing 10 μ/ml bFGF or bFGF plus 1 or 10 μg/ml angiostatin were implanted into the cornea of anesthetized rats. After 7 days, the animals were sacrificed and corneal vessels were stained with colloidal carbon and corneas were examined for angiogenic activity.

B. Results

1. Angiostatin Generation By Conditioned Culture Medium. Incubation of human plasminogen with the SFCM produced by PC-3 cells resulted in the generation of multiple immunoreactive bands at approximately 50 kD (FIG. 1A), similar to those observed by O'Reilly et al. *Cell*, 79, 315–328 (1994). Examination of SFCM from additional cell lines also revealed the generation of the multiple bands, similar to the PC-3 SFCM (data not shown). These cell lines are listed in Table 1 below.

The initial indication that the product was angiostatin was based on the immunoreactivity with the monoclonal antibody specific for kringles 1–3 (K1–3) of plasminogen and the size of the cleavage product that approximated the predicted mass of kringles 1–4 of human plasminogen. Subsequent confirmation that the plasminogen cleavage product was bioactive angiostatin is described below.

Figure 1B:
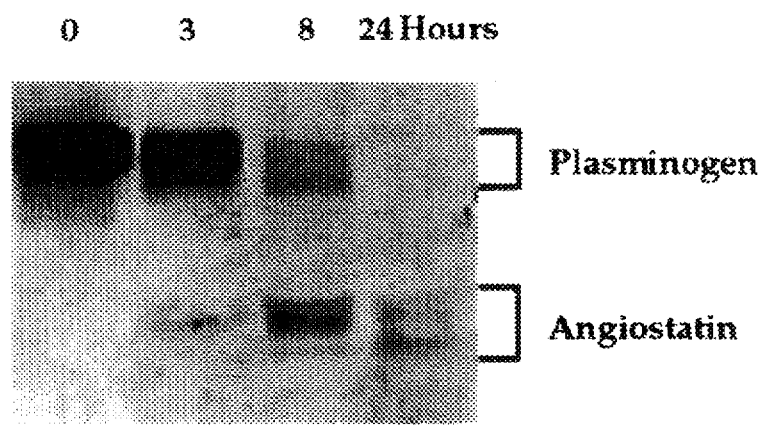
FIG. 1B: Western blot showing that the generation of angiostatin from plasminogen was time dependent. PC-3 SFCM was incubated with plasminogen and, at the timepoints indicated, aliquots were removed and snap frozen prior to western blot analysis. Trace generation of angiostatin was first observed at 3 hours, and complete conversion was noted at 24 hours.
Figure 1C:
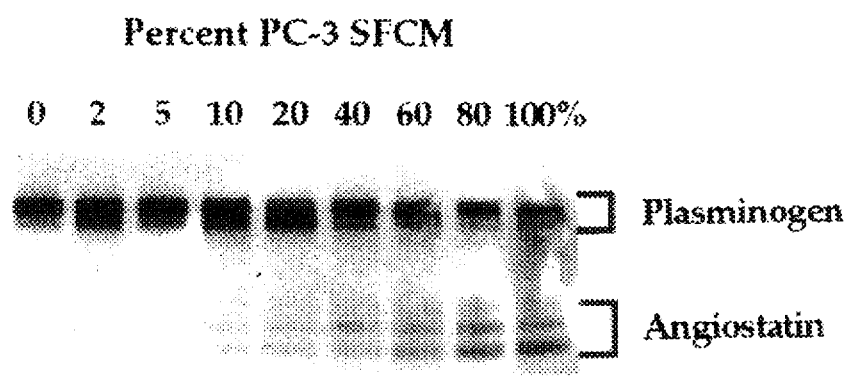
FIG. 1C: Western blots showing that the generation of angiostatin by PC-3 SFCM was concentration dependent. SFCM was diluted with various amounts of fresh RPMI as indicated and incubated with plasminogen for 24 hours.
Figure 1D:
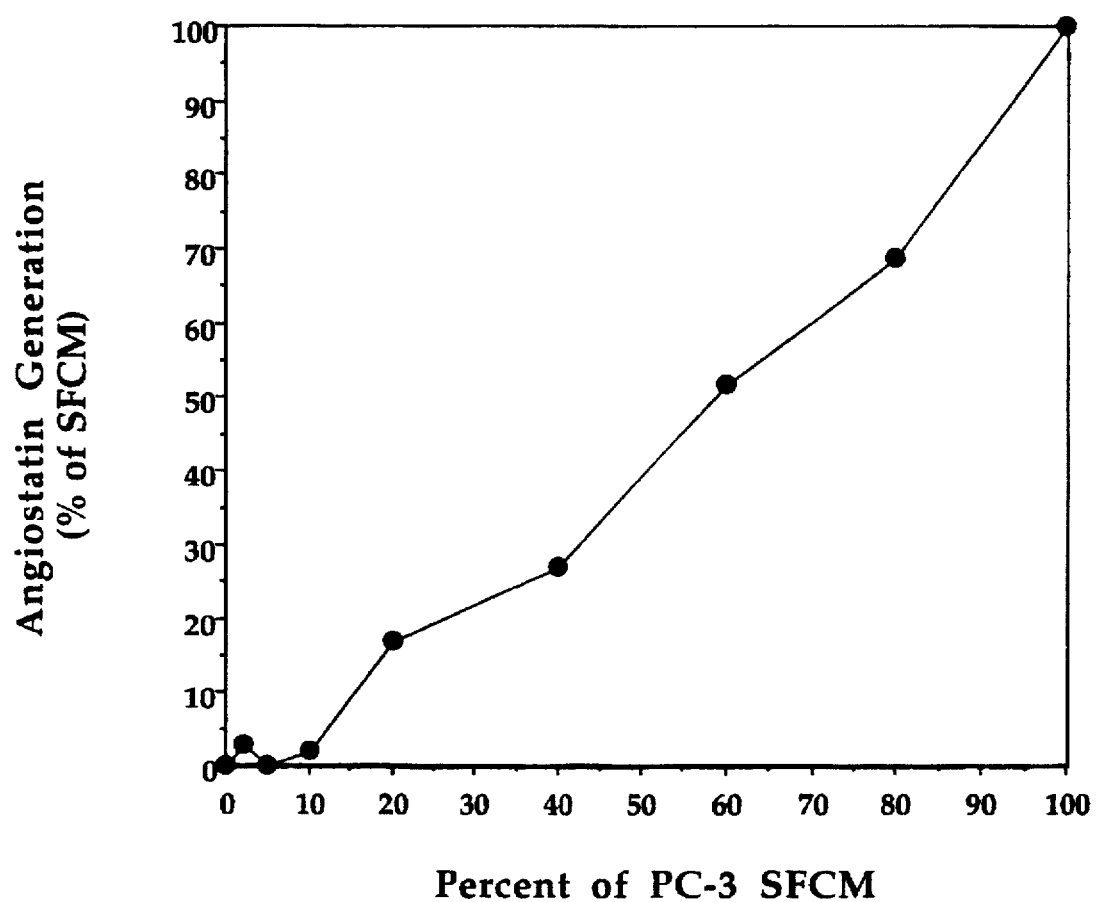
FIG. 1D: Graph illustrating the relationship of angiostatin generation to the amount of SFCM. The relative angiostatin signal was quantitated by scanning densitometer with background subtraction. At 18 hours incubation, there was a linear relationship between the amount of angiostatin generated and the amount of PC-3 SFCM present in the reaction mixture.

Angiostatin generation by PC-3 SFCM was time-dependent. There was a significant decrease in the plasminogen substrate and a corresponding increase in angiostatin beginning at 3 hours, with complete conversion to angiostatin by 24 hours (FIG. 1B). Dilution of the PC-3 SFCM resulted in a proportional decrease in angiostatin generation (FIGS. 1C and 1D).

To determine whether plasmin, the activated form of the zymogen plasminogen, could also be converted to angiostatin, plasmin was evaluated as a potential substrate. Incubation of plasmin with PC-3 SFCM yielded a product indistinguishable from the plasminogen-derived angiostatin (FIG. 1A). In kinetic studies, plasmin was converted to angiostatin at a comparable rate to the plasminogen; 50% conversion by 8 hours, with complete conversion by 24 hours (data not shown). These data suggest that in vitro both plasminogen and plasmin are substrates from which angiostatin can be generation.

TABLE 1

| Cell Lines Tested for Angiostatin-Generating Activity | |
|---|---|
| | Activity |
| Human Prostate Carcinoma | |
| PC-3 | +++ |
| DU-145 | ++ |
| Ln-CaP | + |
| Human Breast Carcinoma | |
| MDA-MB-231 | ++ |
| MCF-7 | +/− |
| Human Glioma | |
| U-373 | + |
| U-118 | + |
| A-172 | ++ |
| U-87 | + |
| Mouse Melanoma | |
| B16F10 | ++ |
| Bovine Smooth Muscle | |
| Primary cell line | ++ |
| Bovine Aortic Endothelial Cells | |
| BAEC | ++ |

2. Enzymatic Class Of Plasminogen-Angiostatin Converting Activity. To determine the proteolytic class of the angiostatin generating activity, PC-3 SFCM was incubated with plasminogen in the presence of various proteinase inhibitors. The proteinase inhibitors were added to the SFCM/plasminogen mix prior to the overnight incubation. Samples were analyzed by western blot for evidence of inhibition of angiostatin generation.

Only serine proteinase inhibitors blocked angiostatin generation (see Table 2 below). By contrast none of the other classes of proteinase inhibitors were effective.

Angiostatin can be generated in vitro by limited proteolysis of plasminogen by elastase. Sottrup-Jensen et al. in *Progress in Chemical Fibrinolysis and Thrombolysis*, 3, 191–209 (Davidson et al. eds. 1978); O'Reilly et al., *Nature Med.*, 2, 689–692 (1996); Dong et al., *Proc. Am. Assoc. Cancer Res.*, 37, 58 (1996). In the present study, angiostatin generation was not inhibited by elastatinal, a specific inhibitor of elastase (see Table 2 below). Additionally, no elastase activity was detected in PC-3 SFCM based on co-incubation of SFCM with 4 elastase-sensitive chromogenic substrates for 24 hours (data not shown). These data indicate that the human plasminogen-angiostatin converting activity is unlikely to depend on the action of an elastase. Furthermore, gelatin zymograms revealed no evidence of active or latent metalloproteinases in the PC-3 SFCM (not shown).

TABLE 2

| Proteinase Inhibitor | Concentration | Class | Inhibitory Activity * |
|---|---|---|---|
| Pefabloc | 4.0 mM | Serine Proteinases | Complete |
| Aprotinin | 0.3 µM | Serine Proteinases | Complete |
| Soybean Trypsin Inhibitor | 2.0 mM | Serine Proteinases | Complete |
| Benzamidine | 1–10 mM | Serine Proteinases | Weak |
| Elastatinal | 50–100 µM | Elastase | None |
| Antipain dihydrochloride | 100 µM | Limited Serine Proteinases | None |
| Leupeptin | 100 µM | Serine and Thiol Proteinases | None |
| Chymostatin | 100 µM | Chymotrypsin | None |
| Bestatin | 10 µM | Aminopeptidases | Weak |
| E-64 | 10 µM | Cysteine Proteinases | None |
| Pepstatin | 1.0 µM | Aspartic Proteinases | None |
| EDTA | 1–10 mM | Metalloproteinases | None |
| 1–10 Phenanthroline | 10 µM | Metalloproteinases | None |
| Phosphoramidon | 100 µM | Metalloproteinases | None |

*Complete inhibition is defined as no immunoreactive angiostatin bands; weak inhibition results in the development of faint angiostatin immunoreactive bands; and none refers to the full generation of angiostatin.

Figure 2:
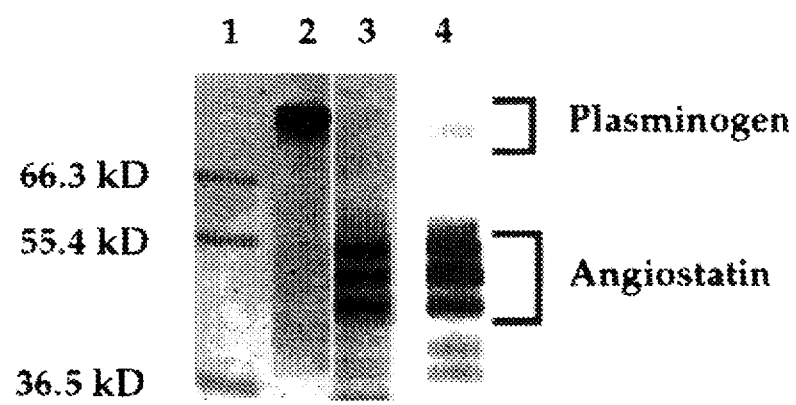
FIG. 2: Western blots after affinity purification of angiostatin generated by incubation of plasminogen with SCFM produced by PC-3 cells. Lane 1, molecular weight standards; lane 2, human plasminogen incubated overnight at 37° C. in non-conditioned RPMI; lane 3, angiostatin produced by incubation of plasminogen with PC-3 SCFM and then affinity purified on lysine-sepharose and detected on western blot by staining with Coomassie blue; lane 4, angiostatin produced by incubation of plasminogen with PC-3 SCFM and then affinity purified on lysine-sepharose and detected on western blot using the monoclonal antibody K1-3 to kringles 1-3.

3. Purification Of Angiostatin. Angiostatin generated by PC-3 SFCM was affinity purified on lysine-sepharose (O'Reilly et al., *Nature Med.*, 2, 689–692 (1996)), and the resulting product examined by western blot and Coomassie blue staining (FIG. 2). The amino-terminal sequence of all three bands was KVYLSECKTG [SEQ. ID NO: 1] that corresponds to residues 78–87 of the plasminogen molecule, confirming that the product was an internal fragment of plasminogen.

4. Angiostatin Generated By PC-3 SFCM Inhibits Angiogenesis. Because angiogenesis represents a cascade of cellular processes that includes endothelial cell proliferation, migration, and tube formation, (Folkman & Shing, *J. Biol. Chem*, 267, 10931–10934 (1992)), multiple in vitro and in vivo assays related to angiogenesis were utilized to confirm that the product generated by incubating plasminogen with PC-3 SFCM was bioactive angiostatin.

Figure 3A:
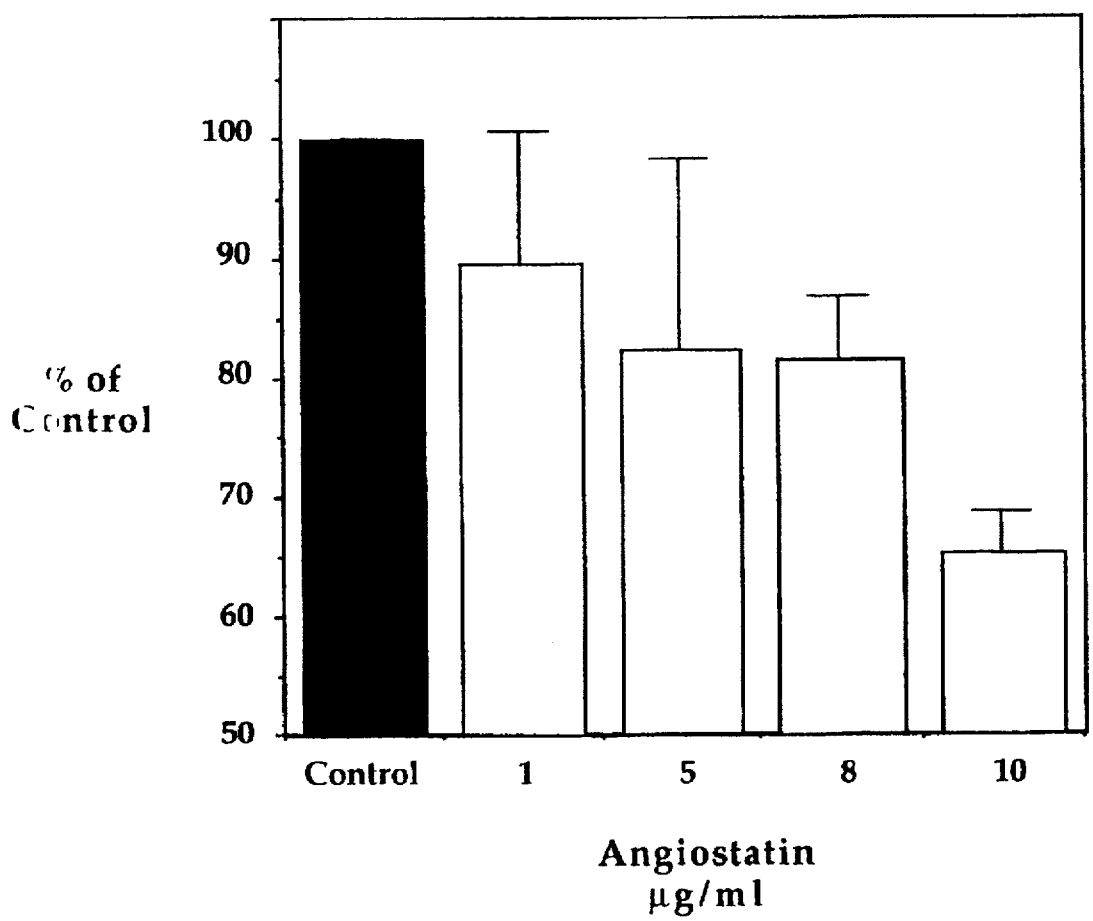

Affinity purified angiostatin generated by PC-3 SFCM inhibited human endothelial cell proliferation in a concentration-dependent manner, with significant inhibition observed at 10 µg/ml ($P<0.05$) in comparison to the non-treated control cell proliferation (FIG. 3A).

Angiostatin generated by PC-3 SFCM also inhibited the bFGF-induced migration of bovine capillary endothelial cells (FIG. 3B) with an $ED_{50}$ of 0.35 µg/ml. The dose/response curve of angiostatin generated by PC-3 SFCM was indistinguishable from that of elastase-generated angiostatin. Inhibition of migration occurred at a 10-fold lower concentration than required to inhibit proliferation, a finding that has been reported for other inhibitors of angiogenesis. Takano et al., *Cancer Res.*, 54, 2654–2660 (1994). This may be due to the fact that the proliferation assay, in contrast to the migration assay, was conducted in RPMI supplemented with 20% calf serum and endothelial cell growth supplement, and therefore contained multiple stimulatory factors.

Figure 4A:
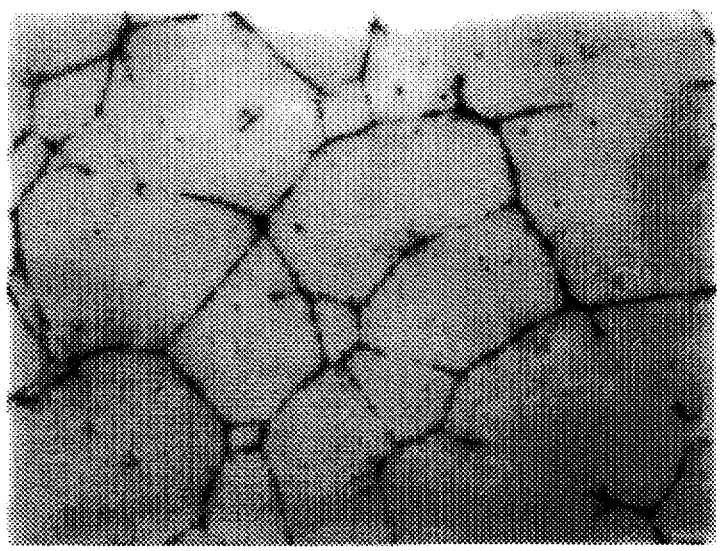
FIGS. 4A-B: Photographs showing that angiostatin produced by incubating plasminogen with PC-3 SCFM inhibits human endothelial cell tube formation in vitro. Human umbilical vein endothelial cells (HUVEC) were plated on gels of Matrigel in 24-well dishes and then were treated with 15 µg/ml of angiostatin produced using PC-3 SFCM in non-conditioned RPMI.
Figure 4B:
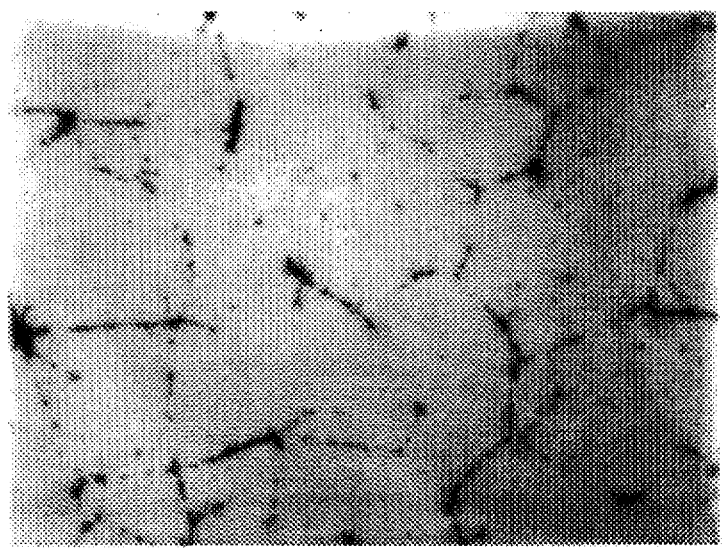

Endothelial cell tube formation on Matrigel was significantly inhibited at 15 µg/ml (FIGS. 4A and B); the mean length of tubes in non-treated control was 674.5±54 mm in comparison to angiostatin produced by PC-3 SFCM, 287.7±47 mm ($P<0.005$).

Figure 5A:
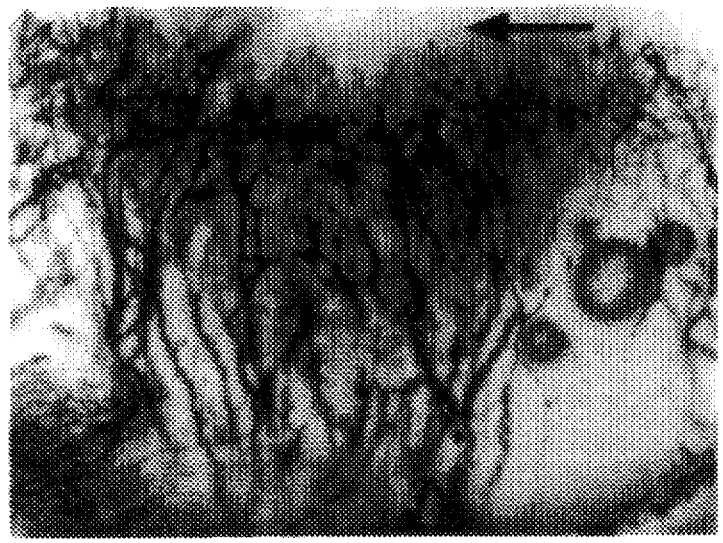
FIGS. 5A-B: Photographs showing the inhibition of angiogenesis in vivo by angiostatin produced using PC-3 SCFM.
Figure 5B:

To determine the effect of angiostatin generated by PC-3 SFCM on corneal angiogenesis in vivo, its ability to block bFGF-induced angiogenesis in the corneal angiogenesis assay was tested. The bFGF pellet induced angiogenesis in 100% of implanted corneas (FIG. 5A). In contrast, angiostatin at 10 µg/ml completely inhibited the bFGF-induced angiogenic response in 3 of 3 animals (FIG. 5B). At a lower dose of 1.0 µg/ml, angiostatin completely blocked angiogenesis in 2 of 3 animals, with partial inhibition in the third animal.

Taken together, these data indicate that the angiostatin generated by the PC-3 SFCM is a potent inhibitor of both in vitro and in vivo angiogenesis.

Example 2: Identification of Factors Responsible For Converting Plasminogen to Angiostatin The human prostate carcinoma cell line PC-3 was grown and PC-3 SFCM was prepared as described in Example 1. Angiostatin was generated by incubation with PC-3 SFCM or other materials identified below as described in Example 1. Western Blots were performed as described in Example 1.

Figure 6:
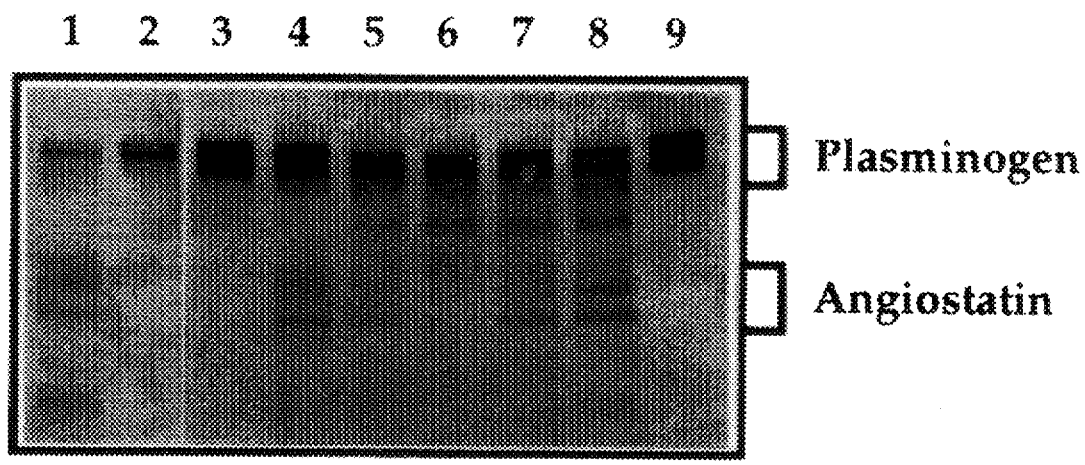
FIG. 6: Western blot showing that the batch eluate from Reactive Red 120-Agarose generates angiostatin when combined with Reactive Red 120-Agarose flow-through, RPMI or RPMI amino acids. Lane 1 — SFCM + plasminogen; Lane 2 — Reactive Red 120-Agarose flow-through + plasminogen; Lane 3 — Reactive Red 120-Agarose batch eluate after dialysis to TBS + plasminogen; Lane 4 — dialyzed batch eluate + Reactive Red 120-Agarose flow-through + plasminogen; Lane 5 — dialyzed batch eluate + RPMI + plasminogen; Lane 6 — dialyzed batch eluate + RPMI vitamin mix + plasminogen; Lane 7 — dialyzed batch eluate + RPMI amino acid mix + plasminogen; Lane 8 —dialyzed batch eluate + RPMI vitamin mix and amino acid mix + plasminogen; Lane 9 — plasminogen + unconditioned RPMI.

PC-3 SFCM was applied to a Reactive Red 120-Agarose column (Sigma Chemical Co.). The flow-through had no residual plasminogen-angiostatin generating activity (PACA) as demonstrated by western blot analysis (FIG. 6). The bound material was eluted with 1 M KCl according to the manufacturer's protocol, then dialyzed to Tris-buffered saline (TBS, 20 mM Tris, pH 7.4, 100 mM NaCl), with a molecular cut-off of 6000–8000 Dalton. PACA was not detected in the dialyzed fraction (FIG. 6). The observation that PACA was not detected in either the flow-through or the eluate led to the hypothesis that two or more factors are necessary to generate angiostatin from plasminogen or plasmin, and that the factors were separated by the Reactive Red 120-Agarose chromatography, with one or more factors being present in the elaute and one more factors being contained in the flow-through.

To test this hypothesis, the dialyzed eluate was recombined with the flow-through. The recombined materials were able to convert plasminogen into angiostatin. Supplementation of the eluate with fresh RPMI culture medium, as well as the Reactive Red 120-Agarose flow-through, restored the capacity of the eluate to generate angiostatin, suggesting that the necessary factor was a component of RPMI, and not a protein or other factor unique to the SFCM.

To further define the putative cofactor, the individual components of RPMI were evaluated for the ability to complement the Reactive Red 120-Agarose eluate. The cofactor was present in the RPMI amino acid mix (FIG. 6).

To determine which amino acid was capable of restoring PACA to the Reactive Red 120-Agarose eluate, the 20 amino acids found in RPMI were tested individually. L-cysteine was the only amino acid capable of restoring PACA to the Reactive Red 120-Agarose eluate (data not shown).

Because the addition of L-cysteine to the Reactive Red 120-Agarose eluate restored angiostatin generating activity, it was hypothesized that the cofactor was a sulfhydryl donor. Pharmacological reducing agents, D-penicillamine and captopril were therefore examined for the ability to restore PACA to the Reactive Red 12-agarose eluate. Addition of 100 μM D-penicillamine to the Reactive Red 120-Agarose eluate restored angiostatin generating activity. Captopril also restored angiostatin generating activity to the Reactive Red 120-Agarose eluate.

PC-3 SFCM was diluted to 50 mM Tris, pH 10.0, 20 mM NaCl and applied to a Hi-Q Sepharose anion exchange resin (Bio Rad). No PACA was detected in the flow-through.

Figure 7:
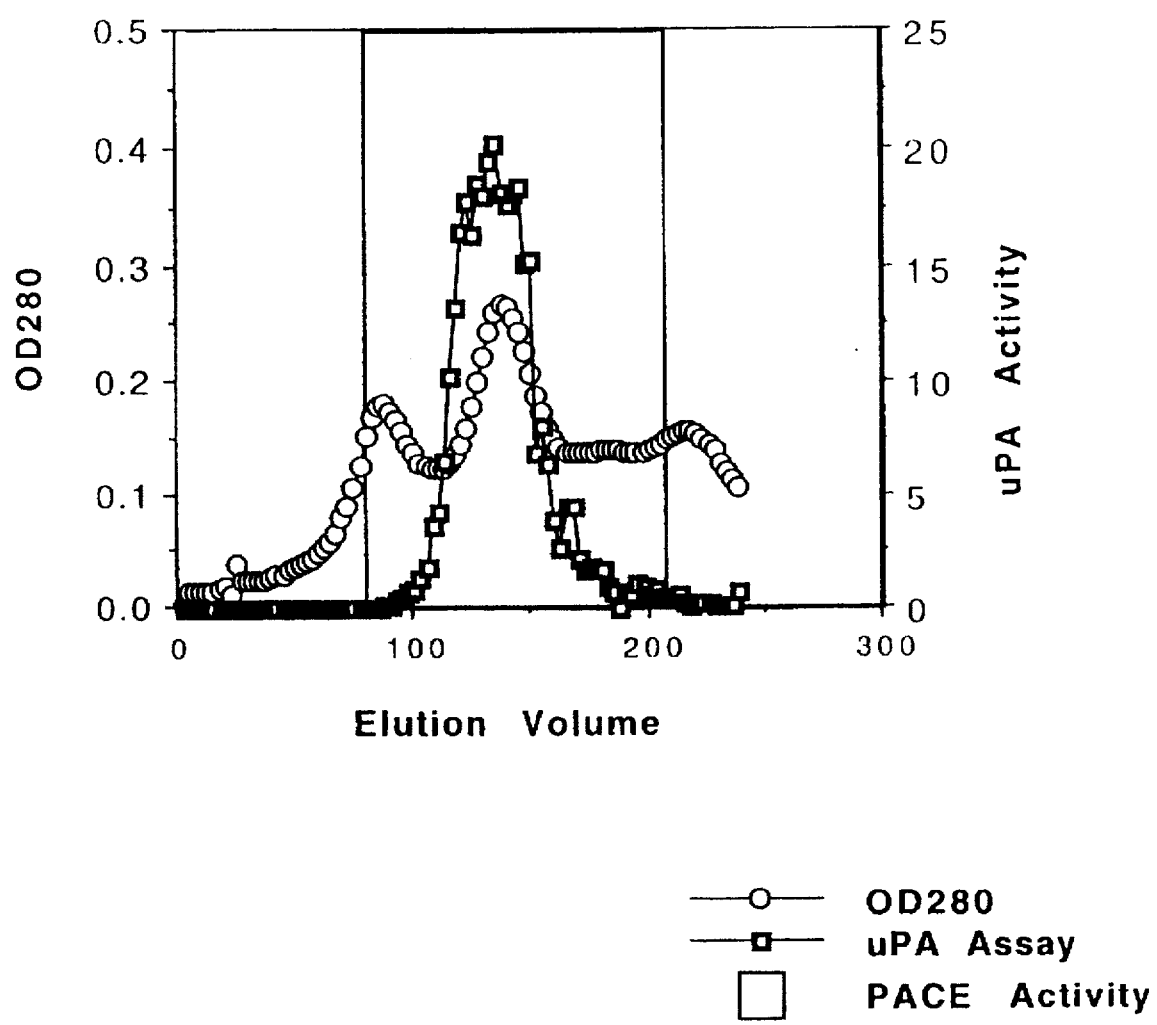
FIG. 7: Graph showing that urokinase-type plasminogen activator (u-PA) activity and plasminogen-angiostatin converting activity (PACA) co-elute on a gradient elution from Hi-Q anion exchange column. Optical density readings at 280 nm demonstrated several protein peaks. u-PA activity was determined by measuring the cleavage of a chromogenic peptide substrate for plasmin (Val-Leu-Lys p-NA) at 405 nm. The peak fractions were assayed for PACA by western blot.

(FIG. 7). Examination of the Reactive Red 120-Agarose eluate revealed it also contained u-PA.

As noted in Example 1, the $NH_2$-terminal cleavage of angiostatin is at $Lys^{77}$, a site that results from cleavage of Glu-plasminogen by plasmin. This suggests that plasmin generation may be a necessary intermediate step in angiostatin generation from plasminogen.

Figure 8:
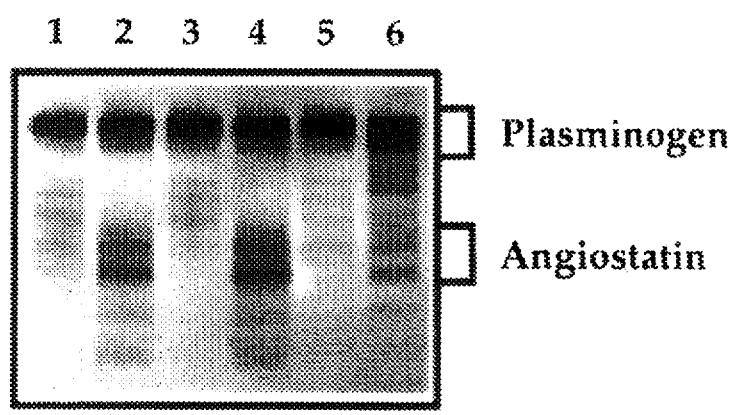
FIG. 8: Western blot showing that addition of u-PA and plasminogen to boiled Reactive Red 120-Agarose flow-through or fresh RPMI medium generated angiostatin. Lane 1 — Reactive Red 120-Agarose flow-through + plasminogen; Lane 2 — Reactive Red 120-Agarose flow-through + plasminogen + u-PA; Lane 3— Reactive Red 120-Agarose boiled flow-through + plasminogen; Lane 4 — Reactive Red 120-Agarose boiled flow-through + plasminogen + u-PA; Lane 5— unconditioned RPMI + plasminogen; Lane 6— unconditioned RPMI + plasminogen + u-PA.

To determine if the factor in the Reactive Red 120-Agarose eluate was u-PA, u-PA was tested as a substitute for the Reactive Red 120-Agarose eluate. As illustrated in FIG. 8, u-PA was capable of generating angiostatin in the presence of boiled Reactive Red 120-Agarose flow-through or RPMI, both sources of sulfhydryl donors. This indicates that the only protein necessary for conversion of plasminogen to angiostatin is u-PA.

Figure 9:
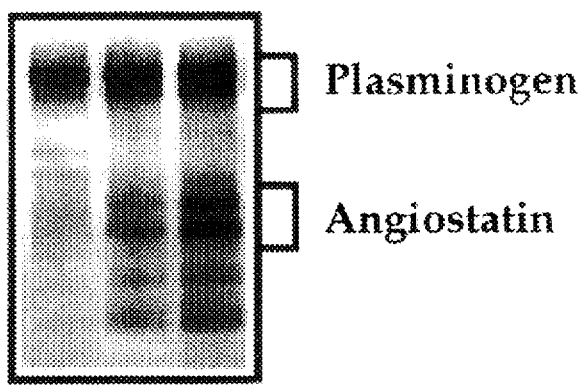
FIG. 9: Western blot showing that the Reactive Red 120-Agarose flow-through produces angiostatin in the presence of plasminogen activators. Lane 1— Reactive Red 120-Agarose flow-through + plasminogen; Lane 2 — Reactive Red 120-Agarose flow-through + plasminogen + u-PA; Lane 3 — Reactive Red 120-Agarose flow-through + plasminogen + t-PA.

Next, u-PA, tissue-type plasminogen activator (t-PA), and streptokinase were tested in combination with the Reactive Red 120-Agarose flow-through for PACA. The plasminogen activators alone failed to generate angiostatin from plasminogen but, in the presence of the flow-through, angiostatin was produced (FIG. 9). These data suggest that plasmin generation is an intermediate for angiostatin generation, and that angiostatin generation is not dependent on which plasminogen activator is present.

Figure 10:
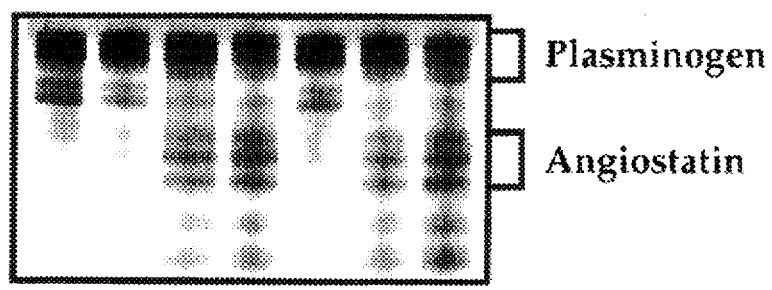
FIG. 10: Western blot showing the production of angiostatin by u-PA and glutathione. Lane 1—plasminogen + u-PA; Lane 2 — plasminogen + u-PA + 5 µM glutathione; Lane 3 — plasminogen + u-PA + 50 µM glutathione; Lane 4 — plasminogen + u-pA + 100 µM glutathione; Lane 5 — plasminogen + u-PA + boiled 5 µM glutathione; Lane 6 — plasminogen + u-PA + boiled 50 µM glutathione; Lane 7 — plasminogen + u-PA + boiled 100 µM glutathione.
Figure 11:
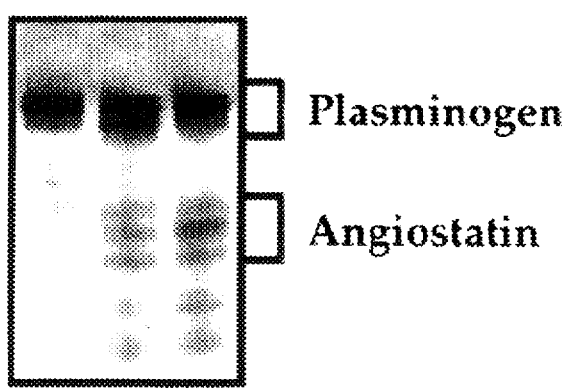
FIG. 11: Western blot showing that the combination of u-PA and D-penicillamine produces angiostatin. Lane 1 — plasminogen + 100 µM D-penicillamine; Lane 2 — plasminogen + u-PA +100 µM D-penicillamine; Lane 3 — plasminogen + u-PA +1.0 mM D-penicillamine.

Having demonstrated that the only protein necessary for conversion of plasminogen to angiostatin is a plasminogen activator and that a sulfhydryl donor is a necessary cofactor, it was next determined if these components are sufficient for angiostatin generation. Incubation of u-PA with plasminogen and at least 5 μM reduced glutathione produced angiostatin (FIG. 10). Use of 100 μM or 1 MM D-penicillamine in combination with u-PA was also capable of generating angiostatin (FIG. 11). These data demonstrate that angiostatin is produced in the setting of plasminogen activation in the presence of physiological (L-cysteine, reduced glutathione) and pharmacological (captopril, D-penicillamine) reducing agents.

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( x i ) SEQUENCE DESCRIPTION: SEQ ID NO:1:

Lys Val Tyr Leu Ser Glu Cys Lys Thr Gly
1               5                   10

Preliminary experiments indicated that PACA eluted from the Hi-Q Sepharose column with 300 mM NaCl. Therefore, the bound material was eluted utilizing a linear gradient from 20 mM to 300 mM NaCl. PACA and urokinase-type plasminogen activator (u-PA) activity were measured in the fractions (after dilution to restore physiological NaCl concentrations). The u-PA activity and PACA co-purified

We claim:

1. A method of generating angiostatin in vitro comprising contacting plasminogen or plasmin with a plasminogen activator and a sulfhydryl donor.

2. The method of claim 1 wherein the plasminogen activator is selected from the group consisting of urokinase, streptokinase, and tissue plasminogen activator.

3. The method of claim 1 wherein the sulfhydryl donor is selected from the group consisting of cysteine, N-acetyl cysteine, captopril, D-penicillamine, and reduced glutathione.

4. The method of claim 1 wherein the angiostatin is at least partially purified from the reaction mixture.

* * * * *